United States Patent [19]

McElfresh

[11] Patent Number: 4,960,240
[45] Date of Patent: Oct. 2, 1990

[54] AIR FRESHENER WITH INTEGRAL TEAR-AWAY TAB

[75] Inventor: Mark W. McElfresh, Burlington, Ky.

[73] Assignee: The Drackett Company, Cincinnati, Ohio

[21] Appl. No.: 341,882

[22] Filed: Apr. 24, 1989

[51] Int. Cl.[5] .............................................. A61L 9/12
[52] U.S. Cl. ......................................... 239/56; 239/57
[58] Field of Search ..................... 422/123; 239/56-59

[56] References Cited

U.S. PATENT DOCUMENTS

| | | | |
|---|---|---|---|
| 2,979,268 | 4/1961 | Brun . | |
| 3,104,816 | 9/1963 | Jaffe | 239/58 X |
| 3,790,081 | 2/1974 | Thornton et al. | 239/59 X |
| 3,797,742 | 3/1974 | Clark et al. | 239/57 |
| 3,964,684 | 6/1976 | Schimanski | 239/56 |
| 4,096,994 | 6/1978 | Bryson | 239/57 |
| 4,258,004 | 3/1981 | Valenzona et al. | 422/123 |
| 4,277,024 | 7/1981 | Spector | 239/34 |
| 4,502,630 | 3/1985 | Haworth et al. | 239/34 |
| 4,610,394 | 2/1982 | Bryson | 239/57 |
| 4,712,739 | 12/1987 | Hecking | 239/58 |
| 4,743,406 | 5/1988 | Steiner et al. | 239/57 X |

*Primary Examiner*—Andres Kashnikow
*Assistant Examiner*—Kevin P. Weldon
*Attorney, Agent, or Firm*—Gene Warzecha

[57] ABSTRACT

An air freshener in the form of a unitary, molded container having a first partial enclosure and a second partial enclosure integrally formed with a hinge therebetween, the partial enclosures having complementary shapes and adapted to be folded about the hinge and sealed together to form a generally flat, hermetically sealed container. The sealed container is adapted to retain an active, vaporizable substance bearing member. One portion of the sealed container is provided with an integrally formed tear-away tab adapted to be removed by a user prior to use of the air freshener.

4 Claims, 1 Drawing Sheet

AIR FRESHENER WITH INTEGRAL TEAR-AWAY TAB

BACKGROUND OF THE INVENTION

1. Field of the Invention

The invention relates generally to dispensers of vaporizable substances. More particularly, the invention relates to air fresheners for dispensing fragrant and/or deodorizing compositions.

2. Description of the Prior Art

Air fresheners for dispensing fragrances, deodorizers and the like are well known and generally comprise a container or shell for retaining a liquid with a wick exposed to ambient or an absorbent pad impregnated with the liquid form of the substance to be dispensed and exposed to ambient. Alternatively, air fresheners may include a solid gelled form of the substance rather than an impregnated pad. In any event, the prior art air fresheners also include some means for sealing the container prior to use so that they may be opened by the consumer as needed.

Air freshener dispensers may be configured in varying degrees of complexity generally dictated by the desired size of the area to be treated, duration of useful life, type of vaporizable substance, aesthetic appearance, etc. The dispensers may have a fixed or variable rate of delivery of the active substance and the dispenser containers are often made of moldable plastic materials. Sealing means to seal the dispenser prior to use may comprise any means compatible with the container of the vaporizable substance, e.g. threaded caps, sealing tape, outer impermeable shipping packages, etc. While there appear to be many known air freshener configurations, there is still a need for an inexpensive air freshener capable of being easily sealed prior to use. All known air fresheners are undesirably costly to manufacture. Examples of some known air fresheners are described below.

U.S. Pat. No. 4,258,004 (Valenzona et al) discloses a type of air freshener containing an absorbent pad impregnated with a scented liquid, the pad being contained within a dispenser having variable size openings and an adhesive means for sticking the dispenser to a desired mounting surface. The air freshener disclosed in this patent comprises a plurality of components which are costly to manufacture and assemble.

U.S. Pat No. 3,964,684 (Schimanski) discloses another type of air freshener having a simpler construction comprising a unitary outer shell provided with a plurality of fixed openings, means for retaining an impregnated pad and means for adhesively securing the air freshener to a mounting surface. While simpler in construction than the Valenzona device, the Schimanski device still requires the manufacture and use of a separate sealing component which must be applied to the air freshener prior to use and removed by the consumer a desired.

U.S. Pat. No. 3,797,742 (Clark et al) shows a simple rectilinear container type air freshener provided with a separate foil seal to be removed prior to use. While seemingly inexpensive, the use of a separate component undesirably increases manufacturing complexity.

U.S. Pat. No. 2,979,268 (Brun) discloses a dispenser which is provided with an integral sealing mechanism which may easily be removed by the consumer prior to use. However, this device also does not lend itself to simplified manufacture and use. The Brun device requires that a plurality of pieces of the package of the dispenser be removed to permit air circulation within the device. Moreover, the Brun device does not enable it to be inobstrusively secured to a mounting surface.

All of the known prior art devices suffer some disadvantage. It is, therefore, an object of this invention to provide an air freshener having a unitary, moldable container provided with an integral sealing means to be opened prior to use.

It is a further object of this invention to provide an air freshener having a minimal number of components which are able to be assembled with a minimal number of manufacturing steps.

SUMMARY OF THE INVENTION

These and other objects of the invention are achieved by the preferred embodiment in the form of an air freshener dispenser comprising: a unitary container comprising a first partial enclosure and a second partial enclosure, said first and second partial enclosures joined along a hinge integrally formed therebetween, said first and second partial enclosures adapted to be folded about said hinge and sealed together to form a hermetically sealed enclosure; at least one of said first or second partial enclosures further comprising: a tear-away tab integrally formed therein, said tear-away tab having, and being defined by, a perimeter thinned a sufficient amount to maintain said enclosure hermetically sealed, so long as said tab remains in place, and to enable a user to remove said tear-away tab from its associated partial enclosure to thereby form an aperture therein and expose the interior of said hermetically sealed enclosure; a member retaining a vaporizable substance to be dispensed into the ambient air, said member adapted to be retained within said hermetically sealed enclosure and exposed through said aperture after said tab is removed; and means integrally formed with one of said first or second partial enclosures for maintaining said aperture in spaced relation to a mounting surface.

DESCRIPTION OF THE PREFERRED EMBODIMENT

Figure 1:
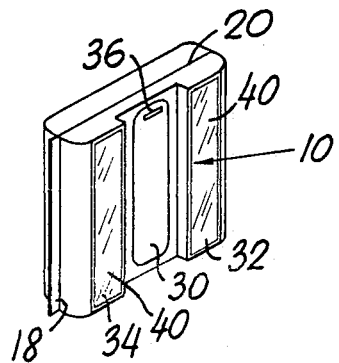
FIG. 1 shows a rear perspective view of an air freshener constructed in accordance with the principles of this invention.

Referring to the FIGS., a fully assembled air freshener 10 constructed in accordance with the principles of the invention is shown in FIG. 1.

Figure 2:
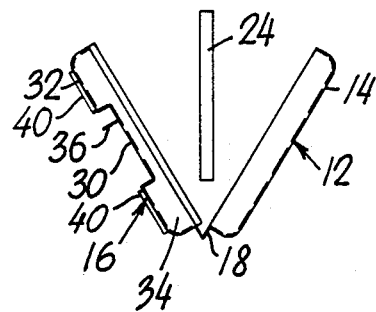
FIG. 2 shows a schematic elevational view of the air freshener of FIG. 1 shown in partially disassembled configuration to show the arrangement of parts.
Figure 3:
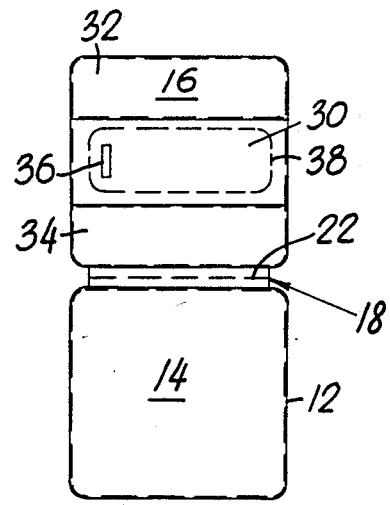
FIG. 3 is a top plan view of the unitary container of the air freshener shown in FIG. 1.

As shown in FIGS. 2 and 3, air freshener 10 comprises a unitary container form 12 having a relatively thin front partial enclosure 14 and a relatively thin rear partial enclosure 16. It will be understood that form 12 is a sheet member which has been molded, vacuum-formed or otherwise suitably shaped into the relatively thin structure shown. While both portions 14 and 16 are shown as having a three-dimensional structure, it will be understood that one or the other of these portions could be flat while the other could be formed. Partial enclosures 14 and 16 are preferably formed with complementary perimeters and adapted to be folded about hinge 18 and sealed along the three-sided perimeter 20 by conventional means. It will be understood by those skilled in the art that container 12 may be molded from any suitable moldable plastic material compatible with the particular vaporizable substance to be retained therein. Hinge 18, while integrally formed with portions 14 and 16 is of lesser thickness and may include a thin score line 22 in order to enable the front and rear partial enclosures 14 and 16 to be folded about line 22. Air freshener 10 includes a member 24 for being retained between front and rear partial enclosures 14 and 16. Member 24 may be a gel containing a suitable fragrant or deodorizing vaporizable material or a pad impregnated with same. After member 24 is inserted between partial enclosures 14 and 16, the two partial enclosures may be sealed along three-sided perimeter 20 thereby hermetically sealing member 24 and any vapors emanating therefrom within air freshener 10.

Front partial enclosure 14 may be integrally formed in or with any desired decorative pattern. Rear partial enclosure 16 is integrally formed with a tear-away tab section 30 and a pair of spaced parallel raised mounting surfaces 32 and 34. It will be understood that either or both partial enclosures 14 or 16 could be provided with a tear-away tab section. Tab 30 is provided with an integral grasping handle 36 protruding outwardly from the surface of tab 30. The perimeter 38 of tab 30 is a thinned portion of rear partial enclosure 16 which serves to define the boundary of tab 30. A user may grasp handle 36 and pull the tab away from rear partial enclosure 16 leaving an aperture conforming generally to the perimeter 38 and exposing the internal member 24.

Adhesive means 40 such as double-back tape, etc. may be applied to raised portions 32 and 34 in order to enable air freshener 10 to be mounted to a mounting surface. It will be understood that once tab 30 is removed and air freshener 10 is secured to a mounting surface, the aperture through which the internal member 24 is exposed will be spaced a distance away from the mounting surface thereby enabling air circulation between raised surfaces 32 and 34, and over member 24 in order to circulate the vapors therefrom into the ambient air.

It will be understood by those skilled in the art that numerous improvements and modifications may be made to the preferred embodiment of the invention disclosed herein without departing from the spirit and scope thereof.

What is claimed is:

1. An air freshener dispenser comprising:

a unitary container comprising a first partial enclosure and a second partial enclosure, said first and second partial enclosures joined along a hinge integrally formed therebetween, said first and second partial enclosures adapted to be folded about said hinge and sealed together to form a hermetically sealed enclosure;

at least one of said first or second partial enclosures further comprising:

a tear-away tab integrally formed therein, said tear-away tab having, and being defined by, a perimeter thinned a sufficient amount to maintain said enclosure hermetically sealed, so long as said tab remains in place, said tab provided with an integral grasping means to enable a user to remove said tear-away tab from its associated partial enclosure to thereby form an aperture therein and expose the interior of said hermetically sealed enclosure;

a member retaining a vaporizable substance to be dispensed into the ambient air, said member adapted to be retained within said hermetically sealed enclosure and exposed through said aperture after said tab is removed; and means integrally formed with one of said first or second partial enclosures for maintaining said aperture in spaced relation to a mounting surface.

2. An air freshener according to claim 1 further comprising:

means for adheringly securing said hermetically sealed enclosure to said surface.

3. An air freshener according to claim 2 wherein said spacing means comprises at least one raised surface integrally formed adjacent said tear-away tab and wherein said adhering means is secured to said raised surface.

4. An air freshener according to claim 2 wherein said spacing means comprises first and second raised surfaces each integrally formed adjacent said tear-away tab and on opposite sides thereof, thereby enabling said aperture to be maintained in spaced relation to said mounting surface after said tab is removed.

* * * * *